United States Patent [19]

Pryor et al.

[11] 4,324,928

[45] Apr. 13, 1982

[54] STABILIZED METHYLCHLOROFORM FORMULATION CONTAINING CYCLOPROPYL METHYL CARBINOL

[75] Inventors: Alvetta Pryor, Houston; Nobuyuki Ishibe, Lake Jackson, both of Tex.

[73] Assignee: The Dow Chemical Company, Midland, Mich.

[21] Appl. No.: 212,649

[22] Filed: Dec. 3, 1980

[51] Int. Cl.$^3$ ............................................. C07C 17/42
[52] U.S. Cl. .................................... 570/118; 252/407
[58] Field of Search ......................... 570/118; 252/407

[56] References Cited

U.S. PATENT DOCUMENTS 3,974,230 8/1976 Archer et al. ...................... 570/118
4,115,461 9/1978 Spencer et al. .................... 570/118

Primary Examiner—Delbert E. Gantz
Assistant Examiner—Joseph A. Boska
Attorney, Agent, or Firm—A. C. Ancona

[57] ABSTRACT

Methylchloroform formulations are stable in the presence of zinc when they contain cyclopropyl methyl carbinol in place of an epoxide as a component of the stabilizer.

3 Claims, No Drawings

STABILIZED METHYLCHLOROFORM FORMULATION CONTAINING CYCLOPROPYL METHYL CARBINOL

BACKGROUND OF THE DISCLOSURE

Methylchloroform is particularly susceptible to decomposition in the presence of metals, especially when aluminum and iron are present. Stabilizers are known which are effective in stabilizing methylchloroform against decomposition induced by contact with iron and aluminum even at elevated temperatures, such as are encountered in vapor degreasing and processes involving purification by distillation.

It is also known, however, that while pure uninhibited methylchloroform at elevated temperatures is relatively inert to the presence of zinc, methylchloroform which is stabilized against decomposition due to contact with other metals, particularly iron and aluminum, tends to decompose badly in the presence of zinc and cause substantial corrosive attack on the zinc metal. Decomposition of the solvent and corrosion of the zinc occur only when the zinc is exposed to the hot vapors of methylchloroform stabilized against iron and aluminum induced decomposition. Zinc below the surface of the boiling solvent will remain virtually unaffected. This is due to the fact that these inhibitors, which stabilized methylchloroform against iron and aluminum, catalyze the attack of methylchloroform on zinc in the boiling vapors of the solvent. This undesirable property causes a restriction of the utility of methylchloroform particularly as a solvent in the vapor degreasing field as galvanized equipment is common and many of the articles to be degreased are zinc or zinc alloy, such as brass or galvanized iron.

An additional need for a stabilized system to render the hot vapors of methylchloroform inert to zinc surfaces is found in the recovery of used solvent. Methylchloroform may be used in the cold degreasing of metals until it becomes saturated with dirt, grease and other impurities from the metal being cleaned. Spent solvent without the stabilizer system hereinafter proposed cannot be recovered by distillation in the zinc-lined stills commonly used in the industry without damage to the lining thereof.

Methylchloroform where used as a vapor degreasing solvent contains minor amounts of certain additives or stabilizers to prevent decomposition of the solvent induced by its contact with metals such as aluminum and iron. Inhibitors such as 1,4-dioxane alone or in combination with nitromethane, secondary butyl alcohol, or monohydric acetylenic alcohols are commonly employed. Such stabilizers are quite effective in rendering the solvent inert to attack of the metal by the degradation products, but greatly increase the ability of zinc, in the boiling solvent vapors, to cause degradation of the solvent and concomitantly increased attack of the metal. This undesirable property of the solvent may be eliminated, however, by the addition thereto of a vicinal monoepoxide in the amount of from about 0.01 to b 5.0 percent by weight of the solvent mixture.

Numerous formulations which contain the epoxide are known to the literature. Thus, for example in U.S. Pat. No. 3,049,571 epoxides are employed together with alcohols, nitroalkanes and dioxane, while in U.S. Pat. No. 3,099,694 an epoxide, together with dioxolane and a monoolefin, is employed as stabilizer for methylchloroform. In U.S. Pat. No. 3,265,747 methylchloroform is stabilized with the combination of a lower dialkyl ketone and an epoxide. More recently U.S. Pat. No. 3,974,230 employs methyl butynol, t-amyl alcohol, a nitroalkane and an epoxide and U.S. Pat. No. 4,115,461 uses dioxane, t-amyl alcohol, an epoxide and a nitroalkane in formulations for stabilizing methylchloroform used in degreasing operations.

It has now been found unexpectedly that the epoxide can be substituted with a particular cycloalkyl carbinol, specifically cyclopropyl methyl carbinol, and achieve the same good stabilized formulation as that requiring the epoxide.

SUMMARY OF THE INVENTION

Cyclopropyl methyl carbinol has been found useful as a substitute for the epoxide in formulations of stabilizers employed to protect methylchloroform in the presence of metals. Such formulations have been found effective in vapor degreasing applications, especially when metals such as aluminum, zinc, copper, and iron are present. Concentration of the carbinol found to be effective are in the range of 0.2 to 1% by volume based on the total of inhibitors and solvent used.

DETAILED DESCRIPTION OF THE INVENTION

As representative examples of formulations useful in stabilizing methylchloroform employed in degreasing are two covered in U.S. Pat. Nos. 3,974,230 and 4,115,461. These contain epoxides and experiments were performed which show that the cyclopropyl methyl carbinol can be effectively substituted for the epoxide in those formulations.

Formulations according to U.S. Pat. No. 3,974,230 may contain from 1.75 to 3.5% 2-methyl-3-butyn-2-ol, 0 to 4.25% of t-amyl alcohol, 0.5 to 2% nitoalkane and 0.5 to 1% of an alkylene oxide, while those according to U.S. Pat. No. 4,115,461 may contain from 1 to 3% dioxane, 1 to 3% t-amyl alcohol, 0.2 to 0.6% nitroalkane and 0.5 to 1% butylene oxide. All above percentages are by volume based on the total volume of solvent and stabilizers.

EXAMPLE 1

A formulation in accordance with each of the above mentioned patents was tested by refluxing the stabilized material and its top and bottom distilled fractions, i.e. fractions of the composition which would correspond to that found in the vapor section and sump section, respectively, of a vapor degreaser. The formulations containing the epoxide and the same formulations in which the cyclopropyl methyl carbinol had been substituted for the epoxide were tested against certain metals. Approximately 430 g of each formulation was partitioned by distillation into 1:1 fractions. Ten milliliter aliquots of both fractions and the nonfractionated solution were refluxed for seven days in the presence of Al-2024, Zn, CU, brass, steel, and iron and the solvent stability was rated.

The formulation according to the '461 patent contained 2.5 vol % dioxane, 1.5 vol % t-amyl alcohol, 0.4 vol % nitromethane and 0.5 vol % cyclopropyl methyl carbinol; and the one according to the '230 patent contained 2.0 vol % 2-methyl-3-butyn-2-ol, 2.0 vol % t-amyl alcohol, 0.4 vol % nitromethane, 0.5 vol % cyclopropyl methyl carbinol. Results are shown in Table I.

TABLE I

| Formulations* | Aluminum Coupon | Aluminum Chips | Zinc Coupon | Zinc Mossy | Ratings** Mossy Zn + Al Chips | Copper | Brass | Steel Wool | Iron Filings |
|---|---|---|---|---|---|---|---|---|---|
| A. Epoxide | | | | | | | | | |
| 1 - '461 | | | | | | | | | |
| a | 0 | 0 | 3 | 0 | 1 | 3 | 3 | 1 | 0 |
| b | 0 | 0 | 3 | 0 | 0 | 2 | 2 | 0 | 0 |
| c | 0 | 0 | 3 | 1 | 1 | 3 | 3 | 1 | 0 |
| 2 - '230 | | | | | | | | | |
| a | 0 | 0 | 0 | 3 | 3 | 0 | 1 | 3 | 0 |
| b | 0 | 0 | 1 | 1 | 4 | 1 | 1 | 4 | 1 |
| c | 0 | 0 | 1 | 4 | 0 | 0 | 2 | 1 | 0 |
| B. Carbinol | | | | | | | | | |
| 3 - '461 | | | | | | | | | |
| a | 0 | 0 | 0 | 0 | 1 | 3 | — | — | — |
| b | 0 | 0 | 3 | 0 | 0 | 1 | 1 | 0 | 1 |
| c | 0 | 0 | 3 | 1 | 1 | 1 | 1 | 1 | 1 |
| 4 - '230 | | | | | | | | | |
| a | 3 | 1 | 2 | 3 | 1 | 0 | 3 | 1 | 3 |
| b | 0 | 0 | 0 | 0 | 1 | 0 | 0 | 2 | 1 |
| c | 0 | 1 | 3 | 1 | 1 | 0 | 0 | 1 | 1 |

*a - unfractionated solution
 b - top fraction
 c - bottom fraction
**The ratings are on a scale of 0-5, zero being substantially no corrosion and clear solvent, while 5 indicates heavy corrosion and discolored, decomposed solvent.

A and B experiments used formulations made with the epoxide and carbinol, respectively, in accordance with U.S. Pat. Nos. 4,115,461 (1 & 3) and 3,974,230 (2 & 4).

We claim:

1. In a stabilizer formulation useful in stabilizing methylchloroform used in vapor degreasing wherein said formulation contains an alkylene oxide as a component of said stabilizer, the improvement which comprises employing cyclopropyl methyl carbinol in place of the epoxide in said formulation.

2. A stabilizer formulation according to claim 1 which contins from 1.75 to 3.5% 2-methyl-3-butyn-2-ol, 0 to 4.25% of t-amyl alcohol, 0.5 to 2% nitroalkane and 0.5 to 1% of cyclopropyl methyl carbinol based on the total volume methylchloroform and stabilizers.

3. A stabilizer formulation according to claim 1 which contains from 1 to 3% dioxane, 1 to 3% t-amyl alcohol, 0.2 to 0.6% nitroalkane and 0.5 to 1% cyclopropyl methyl carbinol based on the total volume of methylchloroform and stabilizers.

* * * * *

UNITED STATES PATENT AND TRADEMARK OFFICE
CERTIFICATE OF CORRECTION

PATENT NO. : 4,324,928
DATED : April 13, 1982
INVENTOR(S) : Alvetta Pryor, and Nobuyuki Ishibe It is certified that error appears in the above—identified patent and that said Letters Patent is hereby corrected as shown below:

Col. 1, line 28, change "stabilized" to --stabilize--.

Col. 1, line 37, change "stabilized" to --stabilizer--.

Col. 1, line 61, delete "b" just before the figure 5.0.

Col. 2, line 30, add the word --operations-- after the word degreasing.

Col. 2, line 38, correct "nitoalkane" to --nitroalkane--.

Col. 2, line 60, correct "CU" to --Cu--.

Col. 4, line 27, correct "contins" to --contains--.

Signed and Sealed this

Third Day of August 1982

[SEAL]

Attest:

Attesting Officer

GERALD J. MOSSINGHOFF
Commissioner of Patents and Trademarks